(12) United States Patent
Bruno et al.

(10) Patent No.: US 8,068,132 B2
(45) Date of Patent: Nov. 29, 2011

(54) **METHOD FOR IDENTIFYING *GUIGNARDIA CITRICARPA***

(75) Inventors: Odemir Martinez Bruno, São Carlos (BR); Mário Augusto Pazoti, São Paulo (BR); José Dalton Cruz Pessoa, São Carlos (BR)

(73) Assignee: Empresa Brasieira de Pesquisa Agropecuaria Embrapa, Brasilia D.F. (BR)

( * ) Notice: Subject to any disclaimer, the term of this patent is extended or adjusted under 35 U.S.C. 154(b) by 657 days.

(21) Appl. No.: 11/912,574

(22) PCT Filed: Apr. 10, 2006

(86) PCT No.: PCT/BR2006/000068
§ 371 (c)(1),
(2), (4) Date: Nov. 28, 2008

(87) PCT Pub. No.: WO2006/113979
PCT Pub. Date: Nov. 2, 2006

(65) Prior Publication Data
US 2009/0167850 A1    Jul. 2, 2009

(30) Foreign Application Priority Data
Apr. 26, 2005   (BR) .................................... 0501535

(51) Int. Cl.
*H04N 5/253* (2006.01)
*H04N 13/00* (2006.01)
(52) U.S. Cl. .......................................... 348/79; 348/42
(58) Field of Classification Search .................. 348/79, 348/42
See application file for complete search history.

(56) References Cited

U.S. PATENT DOCUMENTS

| 6,142,025 A * | 11/2000 | Zborowski et al. ........... 73/865.5 |
| 6,332,034 B1 * | 12/2001 | Makram-Ebeid et al. ..... 382/128 |
| 2002/0154798 A1 * | 10/2002 | Cong et al. .................... 382/128 |
| 2004/0047502 A1 * | 3/2004 | Xu ................................ 382/154 |

* cited by examiner

Primary Examiner — Karen Tang
(74) Attorney, Agent, or Firm — Finnegan, Henderson, Farabow, Garrett & Dunner LLP

(57) ABSTRACT

The present invention refers to a computer vision system for identifying the fungus *Guignardia citricarpa*, the causing agent of the citrus black spot. The invention refers to a method for identifying *Guignardia citricarpa* using a computer vision system comprising the steps of a) image acquisition from a collection disk using a digital camera connected to a microscope b) pre-processing to improve (or correct) the scanned images c) image segmentation to segregate each particle in the image d) analysis and extraction of relevant features of the segmented particles and e) identification using artificial intelligence techniques and artificial neural networks.

3 Claims, 2 Drawing Sheets

METHOD FOR IDENTIFYING *GUIGNARDIA CITRICARPA*

The present invention refers to a computer vision system for identifying the fungus *Guignardia citricarpa*, the agent causing citrus black spot.

Since the process currently used for identifying and counting the spores of the fungus *Guignardia citricarpa*, the agent causing citrus black spot (FIG. 1), is performed manually and, for this reasons is time-consuming and tiring, the artificial vision system was created to help said process.

With the aid of computer techniques, the images obtained from commonly used collection disks were analyzed and the particles found in these images were subjected to an automatic identification process. With this, the present invention shows an alternative to automate said step, as an attempt to help the work developed by the specialist.

A set of techniques for analyzing the images and the characterization of the fungus ascospores based on the shape was studied and compared. Among the techniques, the curvature and the Fourier descriptors show very good results and were used for implementing the computer vision system—CITRUSVIS—that analyzes and identifies the ascospores found in the collection disks images.

Although vision systems similar to the biological vision system will be developed in a very distant future, there are currently mechanisms that perform certain activities more efficiently than the human vision system, for instance. This is the case of measurement systems, biometrics, instrumentation and others.

The artificial vision systems aim to obtain a set of techniques that may support the development of sufficiently effective and reliable products for practical applications in a number of fields. They have been used in several applications, such as the industry, agriculture, medicine and others to perform several tasks.

These systems provided with images analysis and decision-making functions are taking a relevant place in controlling and assuring the quality of products, performing tasks that are usually assigned to human inspectors. In agriculture for instance, the introduction of artificial vision technologies is intended to help the production process, for example, in the management of pests and diseases.

Computer vision techniques capable of characterizing the ascospores of the fungus *Guignardia citricarpa* from microscopic images obtained from the collection disks were used. Additionally, an image analysis tool was developed for identifying eventual spores captured in the disk, identifying and counting the fungus ascospores by using a selected set of techniques that is the object of the present invention.

For developing this system, the computer vision, mathematic morphology, images and signals processing fields were involved, in addition to the biological aspects. This is a multidisciplinary research aiming the agrotechnology field.

A traditional vision system comprises the steps of acquiring, segmenting, extracting features and classification (Gonzalez and Woods, 2002). Among the essential steps in images processing, the segmentation and analysis steps are some of the most important and also more difficult.

A comparative study was conducted with the shapes analysis techniques for characterizing the ascospores. The purpose of this comparison was to evaluate the techniques and select those showing the best performance. In order to conduct this study, a set of samples selected from the images obtained from the collection disks was used. To evaluate/quantify the techniques performance in this set of samples, the classification method based on the minimum distance was employed.

The technique selected was the shape curvature associated with the Fourier descriptors. When compared to the other techniques employed, this technique showed the best result when characterizing and segregating the set of samples.

After selecting the techniques for analyzing and extracting the features, attention was given to the other steps required by a computer vision system. A satisfactory result was obtained by means of a combination among some of them, as occurred in the image segmentation phase.

Since the images contained several particles and did not show to be uniform, the combination of thresholding techniques with non-linear filters and the watershed transform allowed a great number of particles to be correctly segmented.

In the particles identification step, two techniques were used: minimum distance technique and artificial neural networks. The neural network was selected among them due to the satisfactory results obtained.

A prototype of the proposed system was implemented in MATLAB® aiming to test and validate the selected techniques functionality. With this prototype, it was possible to analyze each image by counting the particles identified as ascospores. Further, each of these particles is labeled in the image so that the specialist may visually check the result.

It is worth emphasizing that some images used in the tests have problems that make the analysis difficult, such as: images low quality and resolution and lack of focus that blurred some of them, lack of standardization of the images enlargement factors, and others.

Even with these difficulties, the ascospores identification test result was regarded highly satisfactory (96.6% match), thus meeting the expectations. However, it is believed that this result may be improved by using standardized and enhanced-quality images in a controlled/dedicated acquisition process.

Additionally, this result is only based on the particles subjected to the neural network identification—pre-selected particles in terms of perimeter. If the total of segmented particles is taken into consideration, the match percentage is 99.6%, since the perimeter-based pre-selection eliminates a large number of non-ascospores particles. We must say that these images show a wide range of particles, including those having a shape that is highly similar to an ascospore shape.

Generally, the tested techniques reached match percentages over 60%, a result regarded as positive. Table 1 shows a summary of the results obtained during the techniques comparison. The approach based on the shape curvature showed the best result (approximately 92% match). It is crucial to emphasize that this result was reached when considering only one feature type—the curvature—used as the Fourier descriptors basis.

The curvature has showed a satisfactory result for characterizing the ascospores. Additionally, another feature showed to be useful in this project: the perimeter. Such feature allows samples to be pre-selected. Therefore, part of the non-ascospores particles found in the image is discarded, thus reducing the number of samples to be subjected to the features extraction and identification process.

We must cite that the results submitted and the comparative study are specific to the identification of the *Guignardia citricarpa* ascospores.

TABLE 1

| Experiments | Ascospores | | | Other Particles | | | Totals | |
|---|---|---|---|---|---|---|---|---|
| | Matches | Errors | (% Error) | Matches | Errors | (% Error) | Matches | (% Matches) |
| Moments - signature | 13 | 7 | 35% | 23 | 17 | 43% | 36 | 60% |
| Moments - curvature | 19 | 1 | 5% | 25 | 15 | 38% | 44 | 73% |
| Fourier - contour | 9 | 11 | 55% | 37 | 3 | 8% | 46 | 77% |
| Fourier - signature | 13 | 7 | 35% | 31 | 9 | 23% | 44 | 73% |
| Fourier - projection | 12 | 8 | 40% | 40 | 0 | 0% | 52 | 87% |
| Fourier - curvature | 17 | 3 | 15% | 38 | 2 | 5% | 55 | 92% |
| Wavelets - curvature | 16 | 4 | 20% | 29 | 11 | 28% | 45 | 75% |

The main motivation for developing this system was to create an environment that could allow the conduction of tests using the collection disks images, considering the application of all steps developed (segmentation, features extraction and identification).

Next, the steps involved in the development of the CITRUSVIS system are described, as well as the methods used in each one. The results obtained and the implemented system are showed.

The images used were obtained from the collection disks using digital cameras connected to a conventional microscope. Before acquiring the images, a lactic blue color widely used in microbiology labs was applied on the disks. This color was used for indistinctively staining the hyaline structures (transparent as glass), allowing them to be seen with the aid of a microscope. Both the *Guignardia citricarpa* ascospores and the other spores and hyphae (filamentous parts) from other fungi also captured in the disks are stained.

FIG. 2 shows one of the images obtained from the collection disks. This image shows different particles that are collected in the orchards. Among these particles, an ascospore of the fungus *Guignardia citricarpa* is emphasized.

The images used are in JPEG format (an international standard proposed by the ISO committee—Joint Photographers Expert Group) and show different sizes, most of them 640×512 pitches.

About 70 images were used in the tests. Among them, some of the following problems were found: (i) different colors and shades of the image (disk bottom) and particles, some of them being too clear, thus impairing segmentation, (ii) blurring as a result of the microscope focus inadequate adjustment that, in some cases, changes the particles shape and requires preprocessing for using the image and (iii) low quality due to the JPEG compression.

Initially, the idea was to apply a segmentation that could separate the particles based on the color, since some particles contained in the disks were stained in blue, including the ascospores. The images were converted from RGB to HSI (Rick, 2000) and only component H, referring to the shade, was used to apply thresholding.

The values obtained from the conversion are normalized between 0 and 1 and, considering the interval referring to the blue color, two thresholds were defined, Ti=0.4 and Tf=0.6. Thus, only the particles having a color ranging from cyan to blue (as a result of the color variations due to the dyeing process) were segmented, discarding the remaining particles.

Since the images were compacted in JPEG format, a significant amount of color-related information was discarded and, accordingly, bad results were obtained in the RGB-to-HSI conversion process. Thus, the particles segregation was impaired, creating several noises and deformations in some particles.

Additionally, another problem was the disk bottom color in some images. In some cases, it was not possible to segment the image particles by thresholding, since the image bottom color resulted in a shade within the defined color interval. As most of the images showed some of these problems, this approach was abandoned, since it was not possible to obtain new images with improved quality in time to perform the experiments again.

An alternative to the particles segmentation was to apply a thresholding algorithm directly on the converted image to gray scale. Among the segmentation algorithms, the Otsu algorithm (1979) was chosen due to the good performance observed during the tests conducted with it using the collection disk images. However, noises were generated after the thresholding process as a result of the gray level variation of the images, thus preventing a good segmentation.

A way to reduce the noises contained in the image is to apply image softening filters, such as the Gaussian filter (Gonzalez and Woods, 2002). However, this filter changes the boundary regions due to blurring it causes on the particles edges, thus changing the shape of some of them after the thresholding, in addition to the possibility of increasing the number of connected particles.

It was then decided to apply the non-linear diffusion filter proposed by Perona and Malik (1990). This filter softens the image, preserving the boundary regions. It reduces the gray levels variation per region and consequently the post-thresholding noises (Weickert, 1997). The diffusion equation applied is defined by Perona and Malik (1990) as $$g(\|\nabla I\|) = \frac{1}{1 + \left(\frac{\|\nabla I\|}{K}\right)^2} \quad (1)$$

For applying this filter on image I, the parameter K=4 (boundary threshold) was considered. This parameter indicates the regions regarded as boundaries, that is, for $\|\Delta I\| > K$. In these regions, the diffusion process has decreased effect. On the other hand, $\|\Delta I\| < K$, the diffusion coefficient has a high amplitude and the softening effect will be stronger (Morel and Solimini, 1995; Voci et. al., 2004). Additionally, the number of iterations considered for applying the filter on the disks images was N=30.

When comparing the results obtained by applying the linear and non-linear filters on an image acquired from a collection disk to the respective images after the thresholding, it was noticed that both filters show less noises when compared to the thresholding when directly applied to the original image.

However, by using the Perona-Malik filter, it was noticed that the similarity of the obtained shapes when compared to the original particles is much higher than those obtained using the Gaussian filter. In the image with the Gaussian filter, some particles seem to be larger than they really are or are not seen entirely. It was also observed that the connection among the edges of different particles increased.

Finally, it is critical to emphasize that, although the Perona-Malik filter shows a better result for this test, the computer cost of this technique is higher.

It occurs due to the number of iterations required to obtain a satisfactory result of the diffusion process. Even though, this alternative was adopted for this work, mainly because this filter keeps a similar shape as that obtained after softening with the particle original shape.

By using the Perona-Malik filter, the problems related to noises and gaps in the particles shapes are minimized, but not eliminated. In addition to some noises resulting from the thresholding process, parts of some filaments and other small particles may still appear in the image. For this reason, a morphological filter was applied in order to eliminate the remaining noises.

Another positive aspect concerning the application of the morphological filter is that fact that it softens the particles edges, thus eliminating small peaks in the edges and closing small gaps. For applying the filter, a structurally circular element measuring 5×5 pitches was considered.

Once the image objects are individually analyzed, one of the main difficulties with this kind of image refers to overlapping or connection among the particles. This kind of problem is usually found in images consisting of several elements, like the particles collected in the disks. So as to solve this problem, the watershed mathematic morphology technique (Roerdink and Meijster, 2000) was applied.

The approach adopted for segregating these particles consist in the immersion algorithm proposed by Vincent and Soille (1991). For applying this algorithm, it is necessary to use the Distance Transform (Saito and Toriwaki, 1994) to obtain the distances map, allowing the binarized image to be interpreted as a relief required for applying the watershed transform. With this, all particles start showing depth levels from which the minimum locations for each region are defined.

These minimum locations are used as region markers, so as to avoid problems such as image oversegmentation.

Although there are particles overlapped on the images obtained from the collection disks, some aspects are to be considered. Since this is a binarized image, when there is a group of agglomerated particles, the Distance Transform will not always allow the correct definition of the regions markers relative to the actual arrangement of the particles in the image.

For a group of overlapped particles, the markers were not correctly defined using the distances map and, consequently, the result obtained with the watershed did not correspond to the actual separation among the particles. However, according to disk analysis specialists, the ascospores rarely appear agglomerated with other particles. It was also noticed in the images group used in this project. Overlapping was observed is some images only, but always among a few particles. When connected by a small region, these particles were separated by means of the watershed.

After the segmentation step, each segmented particle is analyzed for the extraction of the corresponding features vectors. In order to carry out this step, an approach based on the shape curvature was employed that, in turn, is obtained from the parametric contour. The steps of contour extraction and descriptors acquisition using the shape curvature are showed below.

For extracting the particles contour, the contour following algorithm (Costa and Cesar, 2000) was applied. However, an adaptation was provided so that the contour of several particles was extracted in the same image, each one being stored in a chained list. It is worth emphasizing that the particles connected to the image edge are discarded, as these particles are usually not complete, that is, part of the shape was lost during the image acquisition.

During the contour extraction, samples from the perimeter were pre-selected. Thus, only those particles having the perimeter within the considered interval (120 to 220 pitches) are analyzed.

Finally, a pre-selected set of contours is extracted from each image so that the descriptors are subsequently extracted.

The descriptors are extracted from the set of contours obtained from each image analyzed. For each of these contours, the curvature is calculated, considering $k(n, \sigma)=F^1\{K(f) \cdot G(f, \sigma)\}$, the Gaussian filter standard deviation being $\sigma=0.22$.

The descriptors are obtained by applying the Fourier Transform on the curvature signal, the spectrum being normalized. Next, 60 descriptors are selected considering only the signal spectral density in the frequency domain (potency spectrum). Thus, each particle obtained from the image is represented by a feature vector and the standards recognition methods are applied on the vectors.

In this step, the purpose was to use standards recognition techniques to validate the discriminating capacity obtained using the shapes description by means of the curvature that, in this work, intended to identify the ascospores of the fungus *Guignardia citricarpa*. When comparing the techniques, the good result obtained using the minimum distance classification led us to choose the curvature as the technique to be applied in the particles description. However, in an attempt to improve the result obtained with this approach, it was decided to use the artificial neural networks.

In order to perform the tests with neural networks, the MATLAB® (Demuth and Beale, 2003) neural networks toolbox was used. In addition to make a graphic interface available for the construction, training and network simulation, this toolbox also allows the network integration with the other steps involved in the vision system, such as the features extraction, thus facilitating the development of the CITRUS-VIS system prototype.

The selected network was a feed-forward backpropagation with 60 inputs, two intermediate layers with 20 and 15 neurons each and an output layer with 2 neurons (FIG. 3).

One of the output layer neurons represents the Ascospores class and the other represents the Other particles class. The neuron having the highest output value indicates the network decision in the class to which the analyzed standard belongs.

For the neural network training, the highest number of samples was considered. These samples were divided into 3 groups: training, validation and test. A total of 300 samples was used, with 60 descriptors each. The samples were divided into 160 samples for training, 70 samples for validation and 70 for test. It is worth emphasizing that the samples are not repeated among the groups, that is, a sample belonging to the training group was not considered for the other groups.

The training algorithm used was Levenberg-Marquardt backpropagation (trainlm) (Demuth and Beale, 2003; Hagan and Menhaj, 1994) and the activation function was the sigmoidal function (logsig), the output interval of which ranges from 0 to 1. The performance obtained during training using the topology (20-15-2) was about 6.9e−8, considering the mean square error (MSE) as a measurement. Other topologies and other training algorithms made available by the toolbox were tested. However, they show lower performance.

The result obtained using the network was very good (98% match), a significant improvement when compared to the result obtained based on the minimum distance between the features vectors (about 92%—see Table 1). It is worth emphasizing that this result was obtained with the pre-selected set of samples for the test.

As mentioned above, the vision system prototype for identifying the ascospores of the fungus *Guignardia citricarpa* was developed in order to provide en environment to perform the tests using the images obtained from the collection disks. Additionally, this environment facilitates the obtained result viewing, marking the identified ascospores in the disk image.

This prototype was developed using MATLAB® graphic interface. This interface was chosen as it easily integrates all developed steps (from the image segmentation to the particles identification using the neural networks). Besides, the environment enables several basic functionalities. FIG. 4 shows the developed prototype interface.

Since the main idea of this system was to build an environment to test and validate the adopted approach, some options were enabled so as to allow the selection of some techniques to be applied during the analysis process. By doing so, it is possible to better compare the results obtained using the combination of different segmentation approaches (linear or non-linear filters and the application of watershed) and identification (based on minimum distance or artificial neural networks).

Besides being showed as a text (number of samples, number of ascospores and time), the results are showed on the image itself, the particles identified as ascospores being marked by a red contour. It is also possible to view the other pre-selected contours (in blue) and also the particles labels (contours list index), as showed in FIG. 4.

In order to validate the adopted solution, the collection disks images were analyzed. Thus, all developed steps were applied, from segmentation to the identification of the particles existing in the disk image. So as to carry out this experiment, 3 image groups were separated, that is, Disk 1 (20 images), Disk 2 (15 images) and Disk 3 (20 images).

Three experiments were carried out, one for each image group. When evaluating the results, the following items were taken into consideration: processing time in seconds; number of segmented particles; number of particles pre-selected by the perimeter; number of errors during the pre-selection (ascospores particles not pre-selected); number of ascospores existing in the image (manually identified); number of ascospores correctly identified by the system; number of false-positives and false-negatives; and the total error, that is, the sum of the errors occurred in the pre-selection and identification by the neural network.

The results obtained using the analysis of each group of images are showed in Tables 2, 3 and 4. These tables include two types of errors: the error referring to the particles pre-selection occurring when the particle of an ascospore is not pre-selected; and the error referring to the neural network that occurs when a pre-selected particle is not correctly classified by the network. In this latter case, the errors are still separated as false-positives and false-negatives, since in this work the occurrence of false-negatives is more significant than the false-positives. Each table also shows a summary of the general result obtained with the corresponding group of images.

TABLE 2

| Images | Time (s) | No. of Samples | Pre-selection Qty. | Pre-selection errors | % Pre-selection errors | Ascospores in the Image | Neural Network Matches | FP | FN | Network errors | % Network errors | % Error per image |
|---|---|---|---|---|---|---|---|---|---|---|---|---|
| disk1_1 | 53 | 90 | 8 | 1 | 11% | 1 | 0 | 0 | 0 | 0 | 0% | 11% |
| disk1_2 | 66 | 148 | 24 | 0 | 0% | 2 | 2 | 1 | 0 | 1 | 4% | 4% |
| disk1_3 | 54 | 94 | 18 | 0 | 0% | 1 | 1 | 0 | 0 | 0 | 0% | 0% |
| disk1_4 | 60 | 121 | 18 | 0 | 0% | 1 | 0 | 0 | 1 | 1 | 6% | 6% |
| disk1_5 | 54 | 81 | 11 | 0 | 0% | 1 | 1 | 0 | 0 | 0 | 0% | 0% |
| disk1_6 | 59 | 120 | 14 | 0 | 0% | 1 | 1 | 0 | 0 | 0 | 0% | 0% |
| disk1_7 | 73 | 179 | 25 | 0 | 0% | 1 | 1 | 0 | 0 | 0 | 0% | 0% |
| disk1_8 | 85 | 219 | 42 | 0 | 0% | 1 | 1 | 2 | 0 | 2 | 5% | 5% |
| disk1_9 | 68 | 132 | 32 | 0 | 0% | 1 | 1 | 1 | 0 | 1 | 3% | 3% |
| disk1_10 | 72 | 173 | 24 | 0 | 0% | 0 | 0 | 1 | 0 | 1 | 4% | 4% |
| disk1_11 | 68 | 159 | 26 | 0 | 0% | 1 | 1 | 0 | 0 | 0 | 0% | 0% |
| disk1_12 | 70 | 168 | 22 | 1 | 4% | 1 | 0 | 0 | 0 | 0 | 0% | 4% |
| disk1_13 | 63 | 137 | 20 | 0 | 0% | 1 | 0 | 1 | 1 | 2 | 10% | 10% |
| disk1_14 | 59 | 119 | 21 | 0 | 0% | 1 | 0 | 1 | 1 | 2 | 10% | 10% |
| disk1_15 | 71 | 177 | 23 | 0 | 0% | 1 | 1 | 0 | 0 | 0 | 0% | 0% |
| disk1_16 | 66 | 136 | 17 | 1 | 6% | 1 | 0 | 1 | 0 | 1 | 6% | 11% |
| disk1_17 | 55 | 104 | 9 | 0 | 0% | 1 | 1 | 0 | 0 | 0 | 0% | 0% |
| disk1_18 | 49 | 71 | 3 | 0 | 0% | 1 | 1 | 0 | 0 | 0 | 0% | 0% |
| disk1_19 | 45 | 53 | 3 | 0 | 0% | 1 | 1 | 0 | 0 | 0 | 0% | 0% |
| disk1_20 | 59 | 110 | 12 | 0 | 0% | 1 | 1 | 0 | 0 | 0 | 0% | 0% |

| General Result | | |
|---|---|---|
| Mean processing time | 62.45 | |
| Total number of pre-selected samples (perimeter) | 372 | |
| Errors during the pre-selection | 3 | 0.8% |
| Errors occurred in the neural network | 11 | 2.96% |
| Total particles (pre-selected + pre-selection errors) | 375 | |
| Total errors (pre-selection + neural network) | 14 | 3.7% |

FP—False-positive
FN—False-negative

TABLE 3

| Images | Time (s) | No. of Samples | Pre-selection Qty. | Pre-selection errors | % Pre-selection errors | Ascospores in the Image | Neural Network Matches | FP | FN | Network errors | % Network errors | % Error per image |
|---|---|---|---|---|---|---|---|---|---|---|---|---|
| disk2_1 | 68 | 173 | 9 | 0 | 0% | 1 | 1 | 0 | 0 | 0 | 0% | 0% |
| disk2_2 | 67 | 157 | 14 | 0 | 0% | 1 | 1 | 1 | 0 | 1 | 7% | 7% |
| disk2_3 | 57 | 105 | 17 | 0 | 0% | 1 | 1 | 0 | 0 | 0 | 0% | 0% |
| disk2_4 | 88 | 245 | 31 | 0 | 0% | 1 | 1 | 1 | 0 | 1 | 3% | 3% |
| disk2_5 | 62 | 138 | 8 | 0 | 0% | 1 | 1 | 0 | 0 | 0 | 0% | 0% |
| disk2_6 | 71 | 176 | 16 | 0 | 0% | 1 | 1 | 0 | 0 | 0 | 0% | 0% |
| disk2_7 | 40 | 15 | 3 | 1 | 25% | 1 | 0 | 1 | 0 | 1 | 33% | 50% |
| disk2_8 | 43 | 39 | 13 | 0 | 0% | 1 | 1 | 0 | 0 | 0 | 0% | 0% |
| disk2_9 | 71 | 171 | 15 | 0 | 0% | 1 | 0 | 0 | 1 | 1 | 7% | 7% |
| disk2_10 | 75 | 178 | 27 | 0 | 0% | 1 | 0 | 0 | 1 | 1 | 4% | 4% |
| disk2_11 | 60 | 126 | 15 | 0 | 0% | 1 | 1 | 0 | 0 | 0 | 0% | 0% |
| disk2_12 | 76 | 163 | 23 | 0 | 0% | 1 | 1 | 0 | 0 | 0 | 0% | 0% |
| disk2_13 | 72 | 175 | 19 | 0 | 0% | 1 | 1 | 0 | 0 | 0 | 0% | 0% |
| disk2_14 | 55 | 106 | 3 | 1 | 25% | 1 | 0 | 0 | 0 | 0 | 0% | 25% |
| disk2_15 | 79 | 217 | 11 | 0 | 0% | 1 | 1 | 0 | 0 | 0 | 0% | 0% |

General Result

| | | |
|---|---|---|
| Mean processing time | 65.6 | |
| Total number of pre-selected samples (perimeter) | 224 | |
| Errors during the pre-selection | 2 | 0.9% |
| Errors occurred in the neural network | 5 | 2.2% |
| Total particles (pre-selected + pre-selection errors) | 226 | |
| Total errors (pre-selection + neural network) | 7 | 3.1% |

FP—False-positive

FN—False-negative

TABLE 4

| Images | Time (s) | No. of Samples | Pre-selection Qty. | Pre-selection errors | % Pre-selection errors | Ascospores in the Image | Neural Network Matches | FP | FN | Network errors | % Network errors | % Error per image |
|---|---|---|---|---|---|---|---|---|---|---|---|---|
| disk3_1 | 47 | 17 | 9 | 0 | 0% | 7 | 7 | 0 | 0 | 0 | 0% | 0% |
| disk3_2 | 100 | 35 | 4 | 0 | 0% | 1 | 1 | 0 | 0 | 0 | 0% | 0% |
| disk3_3 | 55 | 48 | 6 | 2 | 25% | 6 | 4 | 0 | 0 | 0 | 0% | 25% |
| disk3_4 | 90 | 15 | 2 | 0 | 0% | 1 | 1 | 0 | 0 | 0 | 0% | 0% |
| disk3_5 | 46 | 12 | 11 | 0 | 0% | 8 | 8 | 0 | 0 | 0 | 0% | 0% |
| disk3_6 | 47 | 20 | 5 | 0 | 0% | 1 | 1 | 0 | 0 | 0 | 0% | 0% |
| disk3_7 | 47 | 18 | 1 | 0 | 0% | 1 | 1 | 0 | 0 | 0 | 0% | 0% |
| disk3_8 | 57 | 52 | 16 | 0 | 0% | 1 | 1 | 0 | 0 | 0 | 0% | 0% |
| disk3_9 | 65 | 84 | 16 | 0 | 0% | 1 | 1 | 0 | 0 | 0 | 0% | 0% |
| disk3_10 | 53 | 39 | 5 | 0 | 0% | 1 | 1 | 0 | 0 | 0 | 0% | 0% |
| disk3_11 | 62 | 75 | 9 | 0 | 0% | 1 | 1 | 0 | 0 | 0 | 0% | 0% |
| disk3_12 | 100 | 65 | 8 | 0 | 0% | 1 | 0 | 0 | 1 | 1 | 13% | 13% |
| disk3_13 | 165 | 203 | 22 | 1 | 4% | 1 | 0 | 1 | 0 | 1 | 5% | 9% |
| disk3_14 | 71 | 186 | 19 | 0 | 0% | 0 | 0 | 0 | 0 | 0 | 0% | 0% |
| disk3_15 | 74 | 118 | 10 | 0 | 0% | 0 | 0 | 0 | 0 | 0 | 0% | 0% |
| disk3_16 | 72 | 108 | 14 | 0 | 0% | 0 | 0 | 0 | 0 | 0 | 0% | 0% |
| disk3_17 | 54 | 45 | 5 | 0 | 0% | 0 | 0 | 0 | 0 | 0 | 0% | 0% |
| disk3_18 | 72 | 112 | 4 | 0 | 0% | 0 | 0 | 0 | 0 | 0 | 0% | 0% |
| disk3_19 | 57 | 57 | 3 | 0 | 0% | 0 | 0 | 0 | 0 | 0 | 0% | 0% |
| disk3_20 | 73 | 114 | 13 | 0 | 0% | 0 | 0 | 1 | 0 | 1 | 8% | 8% |

General Result

| | | |
|---|---|---|
| Mean processing time | 70.35 | |
| Total number of pre-selected samples (perimeter) | 182 | |
| Errors during the pre-selection | 3 | 1.6% |
| Errors occurred in the neural network | 3 | 1.6% |
| Total particles (pre-selected + pre-selection errors) | 185 | |
| Total errors (pre-selection + neural network) | 6 | 3.2% |

FP—False-positive

FN—False-negative

Based on the data obtained when analyzing the 3 image groups, the experiments were subjected to a general evaluation. This evaluation is showed in Table 5.

TABLE 5

General Result (considering the 55 images)

| | | |
|---|---|---|
| Mean processing time | 66.13 | |
| Total number of pre-selected samples (perimeter) | 778 | |
| Errors during the pre-selection | 8 | 1.0% |
| Errors occurred in the neural network | 19 | 2.4% |
| Total particles (pre-selected + pre-selection errors) | 786 | |
| Total errors (pre-selection + neural network) | 27 | 3.4% |

The general result obtained with these experiments was 96.6% match in the particles identification existing in the disk considering the pre-selected particles only. This result was regarded as more than satisfactory, indicating the good performance of the adopted approach for CITRUSVIS. Additionally, the mean processing time for each image was slightly above 1 minute (66 seconds). This time was regarded as satisfactory, since it was obtained by a prototype of the system and performed in Pentium 4, 256 MB RAM microcomputer. Additionally, the prototype consists in MATLAB® scripts that are interpreted.

Among the examples showed, there are both false-positive and false-negative errors. Most of the time, the false-negative error occurred due to particles segmentation problems. The false-positive cases occurred since the particles shape is similar to that of an ascospore or showed a curvature signal similar to the curvature showed by an ascospore.

The result obtained using the selected techniques was regarded as highly satisfactory. It is worth emphasizing that a significant part of this result is due to the particles description by means of the shape curvature from which the Fourier descriptors were extracted. Additionally, the performance obtained with the network also met the expectations due to the number of particles analyzed.

The implementation of the CITRUSVIS system was very positive, since it allowed us to analyze the techniques behavior in each step carried out, as well as the results obtained with each one. It also allowed us to observe the contribution of each technique to the final result. Another relevant aspect regarding the system was the easy handling of the group images and results obtained. Processing time for each image was satisfactory, taking into account the techniques employed in the analysis.

The previously reported results only considered the pre-selected particles within the defined perimeter interval. However, the pre-selection when extracting the particles contour is also regarded as a classification process in which the particles not having the perimeter within the interval considered for the ascospores were discarded, that is, immediately classified as non-ascospores. Thus, when indistinctively considering all segmented particles, the general error percentage obtained was only 0.4%, that is, 99.6% match when classifying the particles (Table 6).

TABLE 6

| Disco | Segmented particles | Errors per disk | % Error |
|---|---|---|---|
| 1 (20 images) | 2591 | 14 | 0.54% |
| 2 (15 images) | 2184 | 7 | 0.32% |
| 3 (20 images) | 1423 | 6 | 0.42% |
| | 6198 | 27 | 0.44% |

The present invention had the main contributions:
Introduction of a solution for detecting the black spot (*Guignardia citricarpa*) disease using the computer vision techniques;
Development of a method for identifying the ascospores of the fungus *Guignardia citricarpa*; this method will help controlling/fighting the black spot disease in orchards;
Comparison among the different computer vision techniques for analyzing the shapes, identifying the advantages and disadvantages of each one, thus helping or offering alternatives to other situations showing similar problems;
Satisfactory result obtained with the combination of different techniques to improve the segmentation process that was based on the thresholding with the application of non-linear filters, in this case the Perona-Malik filter;
Development of the CITRUSVIS prototype based on the studied techniques, thus allowing experiments involving all steps of the system and the identification of the ascospores with very satisfactory results (99.6 %).

BRIEF DESCRIPTION OF THE DRAWINGS

The following figures are part of this application.

Figure 1:
FIG. 1—Ascospore of the *Guignardia citricarpa*.
Figure 2:
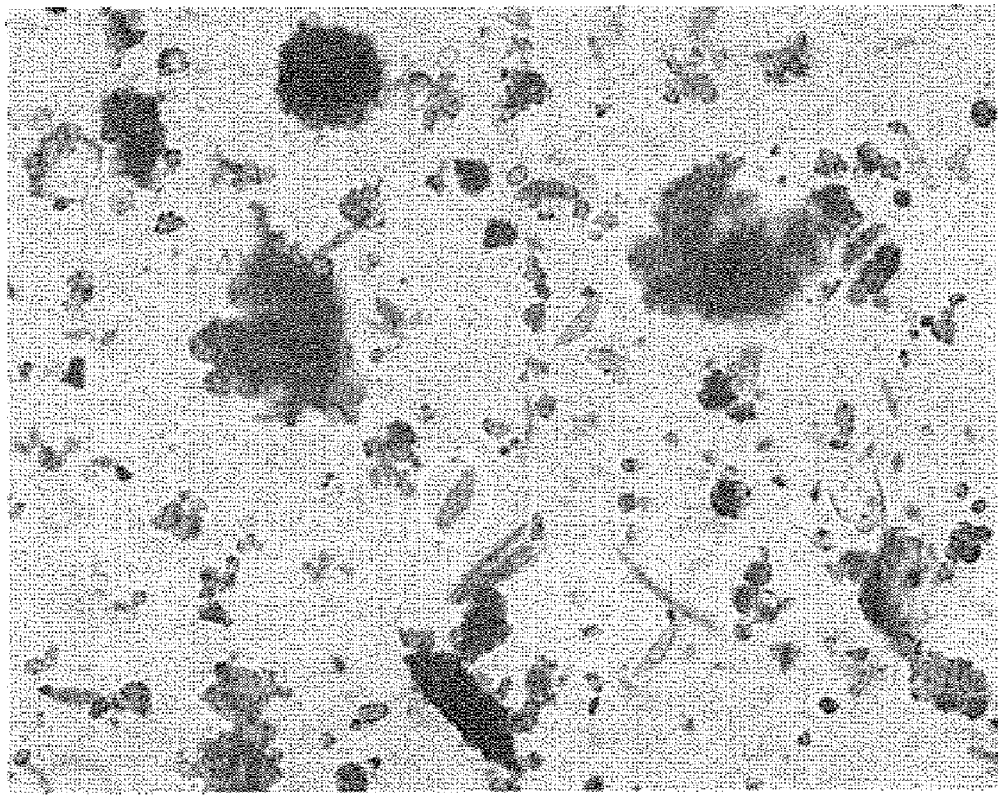
FIG. 2—Digital image acquired from the collection disk enlarged by a microscope.
Figure 3:
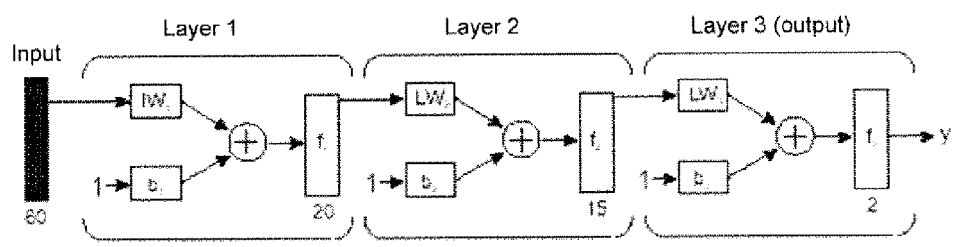
FIG. 3—Topology of the network used in the CITRUSVIS.
Figure 4:
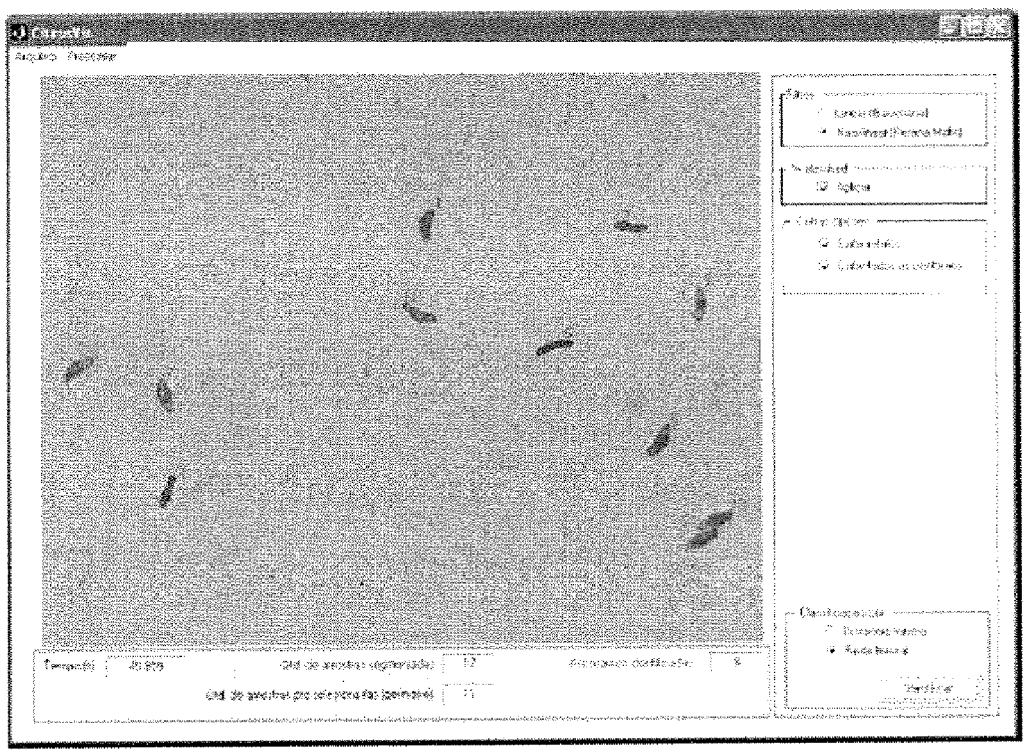
FIG. 4—Interface of the CITRUSVIS prototype.
A search in patent databases did not retrieve methods for the identification of *Guignardia citricarpa* based on the computer vision system, thus evidencing that said system is novel.

The invention claimed is:

1. A method for identifying *Guignardia citricarpa*, characterized in that a scanned image of the ascospore, whether obtained from the capture disk or not, is used in the automatic identification process of *Guignardia citricarpa* by means of the signatures extracted from the fungus images contour.

2. A method for identifying *Guignardia citricarpa*, characterized in that it is performed by means of a computer vision system following the steps below:

a) Image acquisition: the first step of this process consists in the image acquisition from the collection disk using a digital camera connected to a microscope allowing the image enlargement and, as a result, viewing the particles collected in the field, including the ascospores;

b) Pre-processing: this step consists in applying techniques in order to improve (or correct) the scanned images; in this phase, filters are applied mainly for reducing image noises, as well as other anomalies during the image acquisition and that may be corrected by processing the image;

c) Segmentation: in this step, image segmentation techniques are applied in order to segregate each particle in the image; this is required as each particle should be analyzed in order to be identified as ascospores or not; these particles are binarized and the analysis is performed based on the shape;

d) Analysis and extraction of relevant features: in this step, the segmented particles features are individually extracted using image analysis techniques; the particles contour is extracted, as well as the set of signatures related to this contour; from these signatures, the descriptors are calculated and a set of these descriptors is selected to represent each particle being analyzed; the main signatures extracted from the particles shapes include: parametric contour, signature from the distance between the shape contour and centroid, projection and curvature; for obtaining the descriptors, the main techniques were the Fourier descriptors and the wavelets e) Identification: in this step, after the previous step result, the particles are identified using artificial intelligence techniques and artificial neural networks; this step is used for recognizing the ascospores in the image, resulting in their identification and count.

3. The method for identifying *Guignardia citricarpa* according to any preceding claim, characterized in that the signatures used as a basis for the ascospores particles characterization process may include:

a) Parametric contour: consists in X and Y signals referring to the coordinates (x,y) extracted from the shape contour; the contour of each particle is obtained using a contour extracting algorithm, the result of which consists in a list with all coordinates (x,y) referring to the shape boundary (edge);

b) Contour distance to the shape centroid: consists in obtaining a unidimensional signal comprising the distance between each coordinate belonging to the shape contour and the coordinate referring to the particle centroid (center of mass); for obtaining the distance between these coordinates, any algorithm that calculates the distance between two points may be applied;

c) Projection: the signature obtained by the projection consists in traveling along the particle shape in a steady direction (for example, downwards), all points belonging to it in every iteration (that is, every scanned line) being summed; finally, an unidimensional signal is obtained and the shape projection may be obtained in all directions;

d) Curvature: this signature is calculated from the shape contour and refers to the inclination variation of the contour; generally, it describes the concave and convex regions in a shape; the particles are characterized from this description;

all these signatures (unidimensional signals) show variation regarding the size (number of elements composing it); it occurs since the signature size depends on the size (perimeter, area) of the analyzed particle; however, in order to be used for characterizing the particles and subsequently subject them to a recognition process, these signatures must be normalized; for this reason, descriptors extraction methods are applied to these signatures; these methods allow a finite set to be obtained having the same size for all shapes allowing characterization; the techniques applied to these signatures were the Fourier descriptors and the wavelets descriptors.

* * * * *